United States Patent

Templer et al.

[11] Patent Number: 5,312,587
[45] Date of Patent: May 17, 1994

[54] MICROCALORIMETERS

[75] Inventors: Charles Templer; Alexander J. Groszek, both of London, United Kingdom

[73] Assignee: Microscal Limited, London, England

[21] Appl. No.: 743,297

[22] PCT Filed: Feb. 7, 1990

[86] PCT No.: PCT/GB90/00189
§ 371 Date: Jun. 30, 1993
§ 102(e) Date: Jun. 30, 1993

[87] PCT Pub. No.: WO90/09581
PCT Pub. Date: Aug. 23, 1990

[30] Foreign Application Priority Data

Feb. 15, 1989 [GB] United Kingdom ............ 8903454
May 31, 1989 [GB] United Kingdom ............ 8912508

[51] Int. Cl.[5] ........................................ G01N 25/20
[52] U.S. Cl. ............................ 422/51; 422/82.12; 374/1; 374/31
[58] Field of Search ............... 422/51, 82.12, 96; 374/1, 31, 32-34

[56] References Cited

U.S. PATENT DOCUMENTS

| 3,138,436 | 6/1964 | Harmon | 422/51 |
| 3,467,501 | 9/1969 | Groszek | 422/51 X |
| 3,718,437 | 2/1973 | Paloniemi | 422/51 |
| 3,972,681 | 8/1976 | Clack et al. | 422/51 |
| 4,088,447 | 5/1978 | Walker | 422/51 X |
| 4,925,315 | 5/1990 | Bonnard | 422/51 X |

FOREIGN PATENT DOCUMENTS 1366886 9/1974 United Kingdom .
1427780 3/1976 United Kingdom .

OTHER PUBLICATIONS

Perry, R. H. "Teflon Heat Exchangers" in *Perry's Chemical Engineers' Handbook*, 6th ed., pp. 11-24, 1984.

Primary Examiner—James C. Housel
Assistant Examiner—Jeffrey R. Snay
Attorney, Agent, or Firm—Stevens, Davis, Miller & Mosher

[57] ABSTRACT

A sensitive and stable microcalorimeter comprises a cell (1) for a sample of material to be studied and for retaining the sample. The cell walls (2) are of an inert material such as PTFE, and temperature sensors (7) are located within the cell walls at specified positions.

5 Claims, 2 Drawing Sheets

MICROCALORIMETERS

This invention concerns improvements in microcalorimeters. More especially, it concerns a microcalorimeter having a novel temperature sensing arrangement, offering improved stability and effective sensitivity.

Various designs of microcalorimeter are known and are available commercially. A flow microcalorimeter is described in UK Patent GB 1 366 886 and U.S. Pat. No. 3,467,501, the teaching of which is incorporated herein by reference. A particular use of such instruments is in the study of adsorption mechanisms, which may be done by ascertaining heats of adsorption and/or heats of desorption; heats of mixing, dilution, immersion and the like are also important sources of information for scientists and technologists and for the control of industrial processes and product quality.

In the microcalorimeter described in the above-mentioned UK Patent, the temperature changes in a bed of sample positioned within the microcalorimeter cell are detected by two glass-encapsulated thermistors in direct contact with the sample bed and reactants passed into the cell. These thermistors form two arms of a Wheatstone bridge circuit in which the remaining two arms are formed by two identical reference thermistors positioned in a metal block around the microcalormeter cell. Any imbalance in the output of the bridge by a change of temperature in the sample bed produces an electrical signal, which can be measured and evaluated.

Although the above-described arrangement has been very successful for some years, we have now discovered that an arrangement of temperature sensors more particularly described below, offers improved stability and effective sensitivity in the measurement of the very small heat effects studied in microcalorimeters. Accordingly, the present invention provides a microcalorimeter having a sample cell and means for retaining a sample within the cell, characterised in that the cell is of a fluorinated polymer which is insulating, and the cell has an inner wall defining a volume in which a sample may be positioned, and further characterised in that temperature sensing means are located within the polymer forming the cell. The sample in the cell may be placed directly in the form of a powder or granules, or may be inserted in a pre-charged cartridge or other suitable sample holder fitting into the cell. Fluids may then be percolated, either through the samples placed directly in the cell, or via the cartridge, as appropriate. Particularly preferred fluorinated polymers for the cell are PTFE in its various commercially available forms.

It is preferred to use as the temperature sensing means a thermistor, most preferably a pair of thermistors in a Wheatstone bridge circuit. Reference temperature sensors, preferably refence thermistors, are preferably also located within the polymer forming the cell, at a distance from the inner wall greater than that of the temperature sensing means. For example, in a cell formed from PTFE, the internal diameter of the cell may be from 3 to 10 mm, the temperature sensing means is/are located from 200 to 300 um, preferably from 200 to 250 um, from the inner wall, and reference sensors are located from about 1800 to 3000 um, preferably from 2500 to 3000 um, from the inner wall. It is surprising that temperature sensing means located within a material which is an efficient heat insulator should be effective, particularly when used in the preferred embodiments using reference temperature sensors. It will readily be appreciated that other temperature sensing means, for example thermocouples, may be used instead of thermistors.

In a preferred embodiment, a microcalorimeter incorporates an optional calibration unit. Such a unit comprises an electrical resistance heater element, capable of transferring heat to the interior of the cell upon passage of a known quantity of electrical energy, so that the microcalorimeter may be calibrated according to generally known principles. A new calibration unit is, however, unlike previous proposed units, capable of being retained in place during operation, even when strong solvents and corrosive solutions are used. This means that calibration may take place in the presence of the actual sample and fluid being studied, although not during a period when the sample and the fluid interact with a heat effect. The new calibration unit may be generally described as an optional and removeable unit capable of being sealably fitted in the microcalorimeter, and comprising an electrical heating element separated from but not thermally insulated from the interior of the cell. Desirably, the heating element is located within the body of the unit and separated from the interior of the cell by a thin wall. Preferably, the unit is made of a fluorinated polymer identical to that used for the cell. In a more preferred embodiment of the calibration unit, the unit incorporates an outlet tube, having a filter to prevent loss of sample, and desirably heating unit protrudes into the cell.

The invention will now be described with reference to the accompanying drawings, in which.

Figure 1:
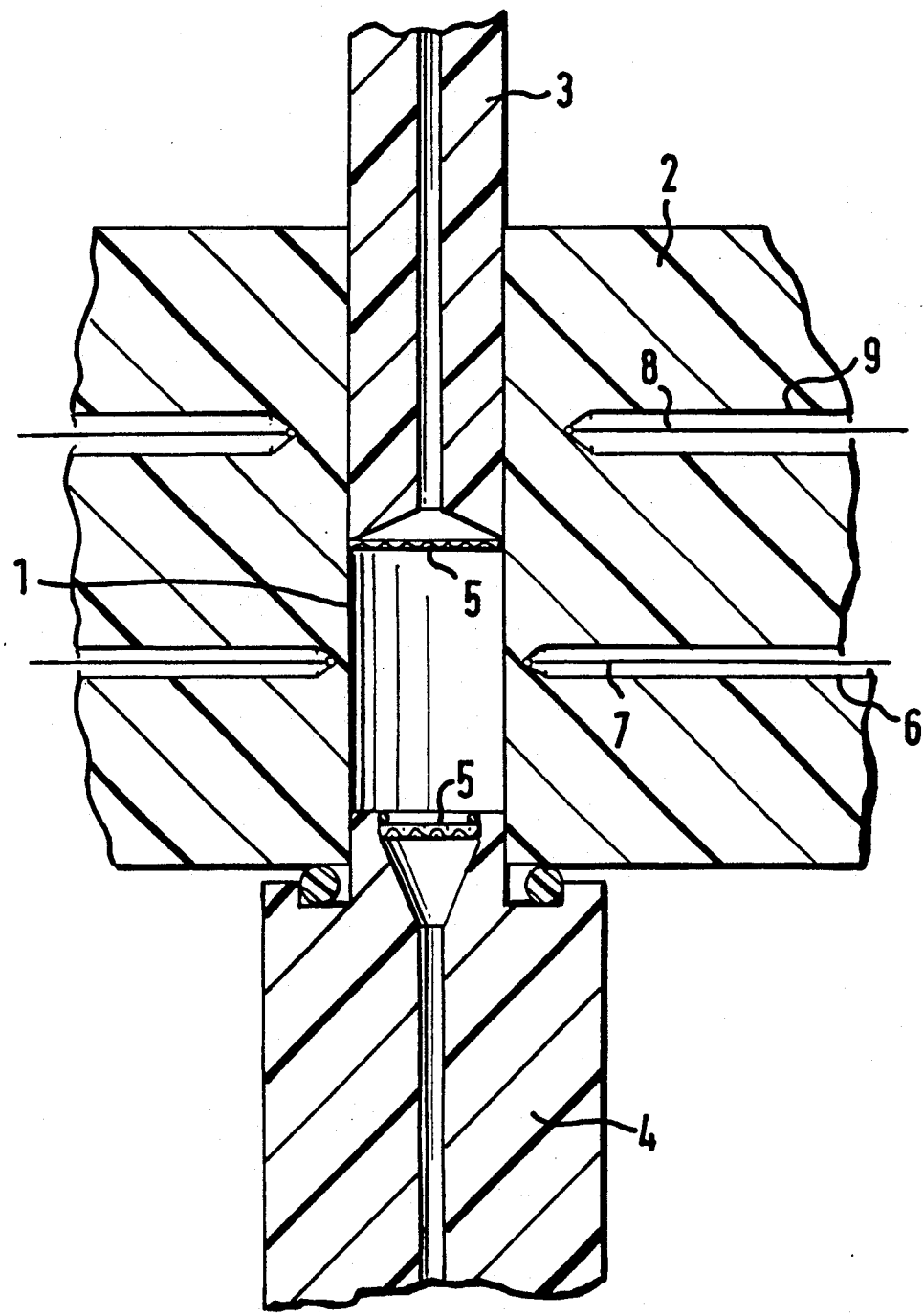
FIG. 1 is a schematic cross-section of a microcalorimeter cell.

Referring to FIG. 1, a microcalorimeter cell is defined by the cylindrical walls, 1, of a cell block, 2, manufactured from PTFE, and having an internal diameter of 6 mm. An inlet tube, 3, which may be of stainless steel or, if more complete inertness is desired, of PTFE, is fitted at one end of the cell. At the other end of the cell is an outlet tube, 4, sealed by an O-ring. Inlet and outlet tubes have filter discs, 5, fitted to prevent loss of solid sample in the cell. The inlet tube is also provided with seals (not shown) to prevent unwanted loss of sample or reactant materials from the cell. Of course, the inlet tube may be used as an outlet tube, and vice versa, should the user wish.

Fitted at the end of carefully machined bores, 6, within the PTFE cell block, are a pair of measuring thermistors, 7. The thermistors are preferably from 200 to 250 um from the inner wall 1. At a distance which is preferably from 2500 to 3000 um from the inner wall, are fitted reference thermistors, 8, in similar machined bores, 9.

The measuring thermistors 7 form two arms of a Wheatstone bridge circuit, the other two arms of which are formed by the reference thermistors, 8. In comparative tests with known microcalorimeters in which the measuring thermistors are positioned within the cell, the arrangement of the invention offered greater stability and accuracy, that is improved effective sensitivity. Other benefits such as increased thermistor life and avoidance of interference from undesired reaction involving the thermistors may be expected to arise from the invention. Another benefit from the new arrangement is the possibility of insertion of a sample in a cartridge, which is especially suitable for samples in the form of thin filaments, foils, consolidated porous materials, felts and sponges.

Figure 2:
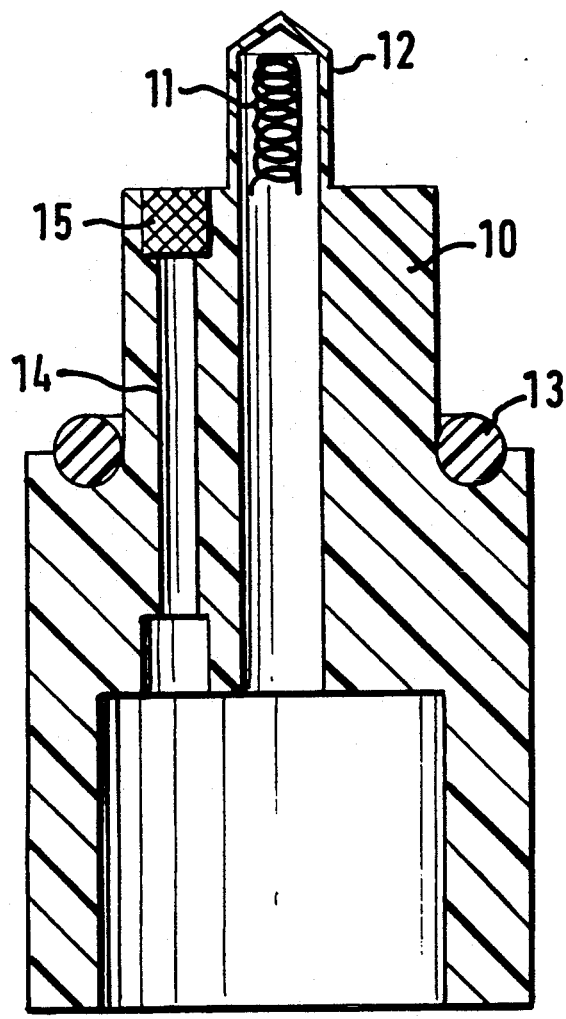
FIG. 2 is a schematic cross-section of a calibration unit suitable for the microcalorimeter cell of FIG. 1.

Referring now to FIG. 2, the calibration unit is manufactured to replace outlet tube 4 in the cell of FIG. 1, and comprises a body part 10. The body part is machined from a block of PTFE, thus providing inertness to sample and to fluid, and effective protection of and sealing of a heating coil, 11, fitted within a bored out protrusion, 12, integral with the body part. An O-ring seal, 13, is fitted within an annular recess to provide sealing against the base of the cell. An outlet tube, 14, has a filter, 15, to prevent loss of sample during operation. A further tube (not shown) may be attached to the end of the outlet tube remote from the filter to remove fluid from the cell. The heating coil 11 is connected to wires (not shown) which pass through the central bore from the coil to a remote control unit (not shown). The thin wall of the protrusion 12 is suitably from 50 to 250 um in thickness, although the lower thickness depends upon the ability to form the protrusion and potential permeability problems.

We claim:

1. A microcalorimeter having a sample cell and means for retaining a sample within the cell, wherein the cell is formed of a fluorinated polymer which is thermally insulating and has an inner wall defining a volume for containing said sample; and further having temperature sensing means embedded within the polymer forming the cell, said temperature sensing means being located a predetermined distance from said inner wall and exterior to said volume.

2. A microcalorimeter according to claim 1, in which the temperature sensing means is located at a distance of from 200 to 300 microns from the inner wall.

3. A microcalorimeter according to claim 2, further including at least one reference temperature sensing means located at a distance of from 1800 to 3000 microns from the inner wall and exterior to said volume.

4. A microcalorimeter according to claim 1 further including a removable calibration unit capable of being sealably fitted in said volume of said cell and comprising an electrical heating element located within the body of the calibration unit and separated from the interior of the cell, when so fitted therein, by a thin wall.

5. A microcalorimeter according to claim 4, wherein the heating element protrudes into the cell.

* * * * *